(12) United States Patent
Kwak et al.

(10) Patent No.: US 9,046,474 B2
(45) Date of Patent: Jun. 2, 2015

(54) MULTI-ANALYZER ANGLE SPECTROSCOPIC ELLIPSOMETRY

(75) Inventors: Hidong Kwak, San Jose, CA (US);
Ward Dixon, Livermore, CA (US);
Leonid Poslavsky, Belmont, CA (US);
Torsten R. Kaack, Los Altos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 117 days.

(21) Appl. No.: 13/541,176

(22) Filed: Jul. 3, 2012

(65) Prior Publication Data

US 2013/0010296 A1    Jan. 10, 2013

Related U.S. Application Data

(60) Provisional application No. 61/505,403, filed on Jul. 7, 2011.

(51) Int. Cl.
*G01J 4/00* (2006.01)
*G01N 21/21* (2006.01)

(52) U.S. Cl.
CPC ........ *G01N 21/211* (2013.01); *G01N 2021/213* (2013.01); *G01N 2021/214* (2013.01)

(58) Field of Classification Search
USPC .......................................................... 356/369
See application file for complete search history.

(56) References Cited

U.S. PATENT DOCUMENTS

| | | | |
|---|---|---|---|
| 3,880,524 A * | 4/1975 | Dill et al. ....................... | 356/369 |
| 4,030,836 A | 6/1977 | Smith | |
| 5,329,357 A * | 7/1994 | Bernoux et al. ............... | 356/369 |
| 5,333,052 A | 7/1994 | Finarov | |
| 5,581,350 A * | 12/1996 | Chen et al. ..................... | 356/369 |
| 5,608,526 A | 3/1997 | Piwonka-Corle et al. | |
| 5,706,088 A * | 1/1998 | Chao et al. ..................... | 356/369 |
| 6,611,330 B2 | 8/2003 | Lee et al. | |
| 6,813,026 B2 | 11/2004 | McAninch | |
| 7,075,650 B1 | 7/2006 | Johs et al. | |
| 2005/0213487 A1* | 9/2005 | Yamamoto et al. ........... | 369/288 |
| 2006/0274310 A1 | 12/2006 | Kandel et al. | |
| 2009/0109438 A1 | 4/2009 | Fukue | |
| 2009/0174883 A1* | 7/2009 | Zawaideh et al. ............. | 356/369 |
| 2011/0176133 A1* | 7/2011 | Dang et al. .................... | 356/369 |

FOREIGN PATENT DOCUMENTS

WO    2010049652 A9    5/2010

OTHER PUBLICATIONS

F. Ferrieu; "Infrared Spectroscopic Ellipsometry Using a Fourier Transform Infrared Spectrometer: Some Applications in Thin-Film Characterization"; Review of Scientific Instruments 60 No. 10, Oct. 1989; copyright 1989 American Institute of Physics; pp. 3212-3216.
European Search Report mailed Feb. 17, 2015; European Patent Office (EPO); EP application No. 12807285.7 claiming priority to PCT/US12/45436; Applicant: KLA-Tencor Corporation; 9 pages.

* cited by examiner

*Primary Examiner* — Tarifur Chowdhury
*Assistant Examiner* — Omar Nixon
(74) *Attorney, Agent, or Firm* — Suiter Swantz pc llo

(57) ABSTRACT

Ellipsometry systems and ellipsometry data collection methods with improved stabilities are disclosed. In accordance with the present disclosure, multiple predetermined, discrete analyzer angles are utilized to collect ellipsometry data for a single measurement, and data regression is performed based on the ellipsometry data collected at these predetermined, discrete analyzer angles. Utilizing multiple discrete analyzer angles for a single measurement improves the stability of the ellipsometry system.

18 Claims, 4 Drawing Sheets

MULTI-ANALYZER ANGLE SPECTROSCOPIC ELLIPSOMETRY

CROSS-REFERENCE TO RELATED APPLICATIONS

The present application claims the benefit under 35 U.S.C. §119(e) of U.S. Provisional Application Ser. No. 61/505,403, filed Jul. 7, 2011. Said U.S. Provisional Application Ser. No. 61/505,403 is hereby incorporated by reference in its entirety.

TECHNICAL FIELD

The disclosure generally relates to the field of surface inspection, and particularly to ellipsometry tools.

BACKGROUND

Thin polished plates such as silicon wafers and the like are a very important part of modern technology. A wafer, for instance, may refer to a thin slice of semiconductor material used in the fabrication of integrated circuits and other devices. Other examples of thin polished plates/films may include magnetic disc substrates, gauge blocks and the like. While the technique described here refers mainly to wafers, it is to be understood that the technique also is applicable to other types of polished plates and films as well. The term wafer and the term thin polished plate and/or film may be used interchangeably in the present disclosure.

Generally, certain requirements may be established for the dielectric properties of the wafers. Ellipsometry is an optical technique for the investigation of the dielectric properties of the wafers. Upon the analysis of the change of polarization of light, which is reflected off a sample (e.g., a wafer surface), ellipsometry can yield information about the sample. Ellipsometry can probe the complex refractive index or dielectric function tensor, which gives access to fundamental physical parameters and is related to a variety of sample properties, including morphology, crystal quality, chemical composition, or electrical conductivity. Ellipsometry is commonly used to characterize film thickness for single layers or complex multilayer stacks ranging from a few angstroms or tenths of a nanometer to several micrometers.

Spectroscopic ellipsometry is a type of ellipsometry that employs a broad band light source, which covers a certain spectral range (e.g., in the infrared, visible or ultraviolet spectral region). By covering a spectral range, the complex refractive index or the dielectric function tensor in the corresponding spectral region can be obtained, which gives access to a large number of fundamental physical properties.

However, testing results indicate that measurements obtained by the existing ellipsometry tools are not stable under certain circumstances. Therein lies a need for a ellipsometry tool with improved measurement stability.

SUMMARY

The present disclosure is directed an ellipsometry system. The ellipsometry system may include a support mechanism configured for supporting a wafer and an illumination source configured for delivering an incident beam towards the wafer. The incident beam may reflect off the wafer thereby forming a reflected beam. The ellipsometry system may also include an analyzer configured for polarizing the reflected beam. The polarization direction of the analyzer may be rotatable to a plurality of predetermined, discrete angular positions. A detector may be utilized to collect a set of spectrum data based on the reflected beam passing through the analyzer. Each spectrum data of the set of spectrum data being collected may correspond to one of the set of predetermined, discrete angular positions. Once the set of spectrum data is collected, a processor module may be utilized to perform simultaneous regression on the set of spectrum data.

A further embodiment of the present disclosure is directed to an ellipsometry method for inspecting a wafer. The method may include: delivering an incident beam towards the wafer, wherein the incident beam reflects off the wafer thereby forming a reflected beam; polarizing the reflected beam utilizing an analyzer, the analyzer having a polarization direction rotatable to a set of predetermined, discrete angular positions; collecting a set of spectrum data based on the reflected beam passing through the analyzer, each spectrum data of the set of spectrum data being collected when the polarization direction of the analyzer is pointing to one of the set of predetermined, discrete angular positions; and performing simultaneous regression on the set of spectrum data collected.

An additional embodiment of the present disclosure is also directed to an ellipsometry method for inspecting a wafer. The method may include: delivering an incident beam towards the wafer, wherein the incident beam reflects off the wafer thereby forming a reflected beam; polarizing the reflected beam utilizing an analyzer, the analyzer having a polarization direction pointing to a first predetermined, discrete angular position; collecting the reflected beam passing through the analyzer when the polarization direction of the analyzer is pointing to the first predetermined, discrete angular position; rotating the analyzer, wherein the polarization direction of the analyzer is rotated to point to a second predetermined, discrete angular position; collecting the reflected beam passing through the analyzer when the polarization direction of the analyzer is pointing to the second predetermined, discrete angular position; and performing simultaneous regression on spectrum data collected when the polarization direction of the analyzer is pointing to the first predetermined, discrete angular position and when the polarization direction of the analyzer is pointing to the second predetermined, discrete angular position.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

The present disclosure is directed to ellipsometry systems and ellipsometry data collection methods with improved stabilities. In accordance with the present disclosure, multiple predetermined, discrete analyzer angles are utilized to collect ellipsometry data for a single measurement, and data regression is performed based on the ellipsometry data collected at these predetermined, discrete analyzer angles. Utilizing multiple discrete analyzer angles for a single measurement improves the stability of the ellipsometry system.

Figure 1:
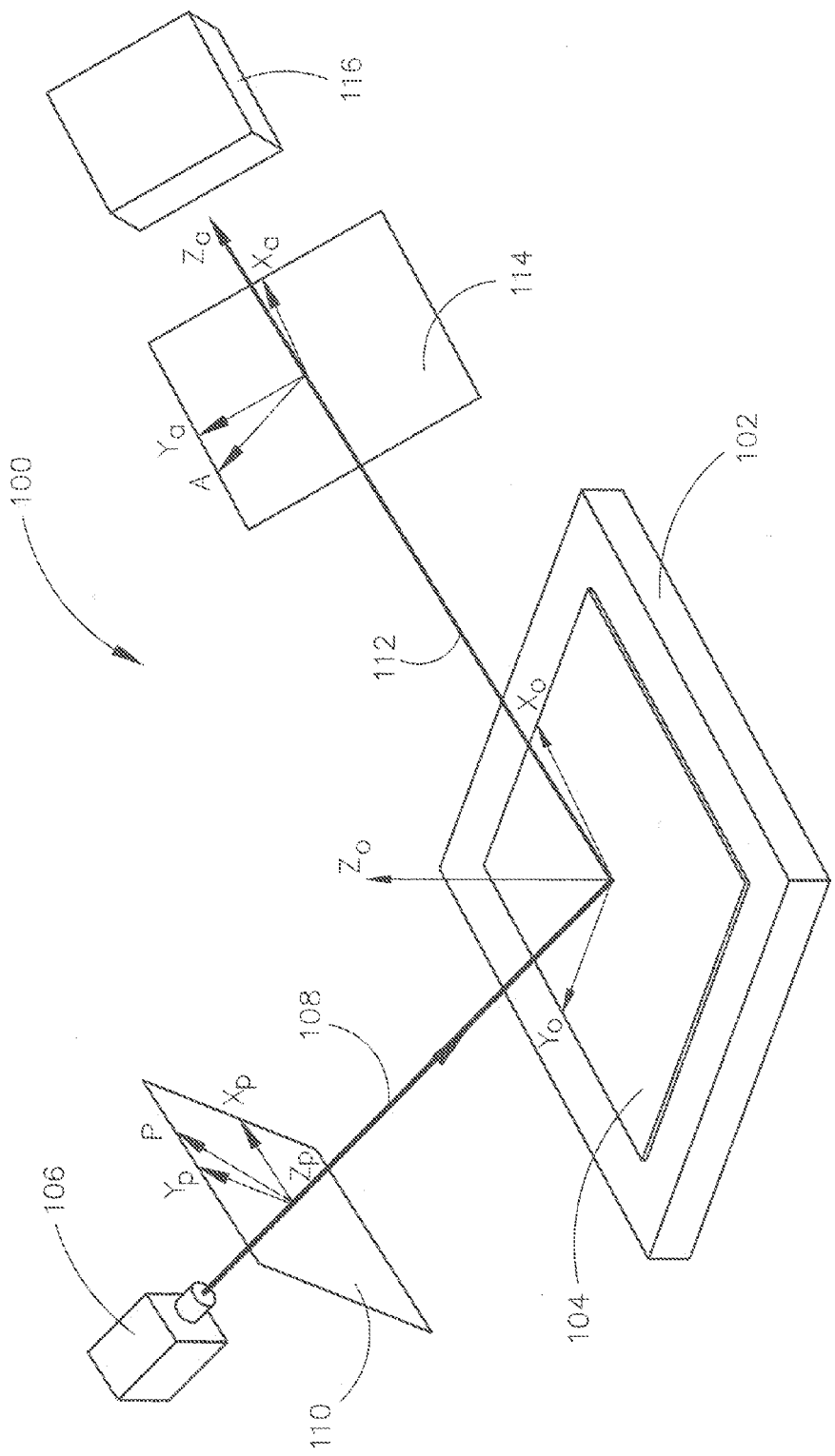
FIG. 1 is an isometric view of an illustration depicting an ellipsometry system in accordance with the present disclosure.
Figure 2:
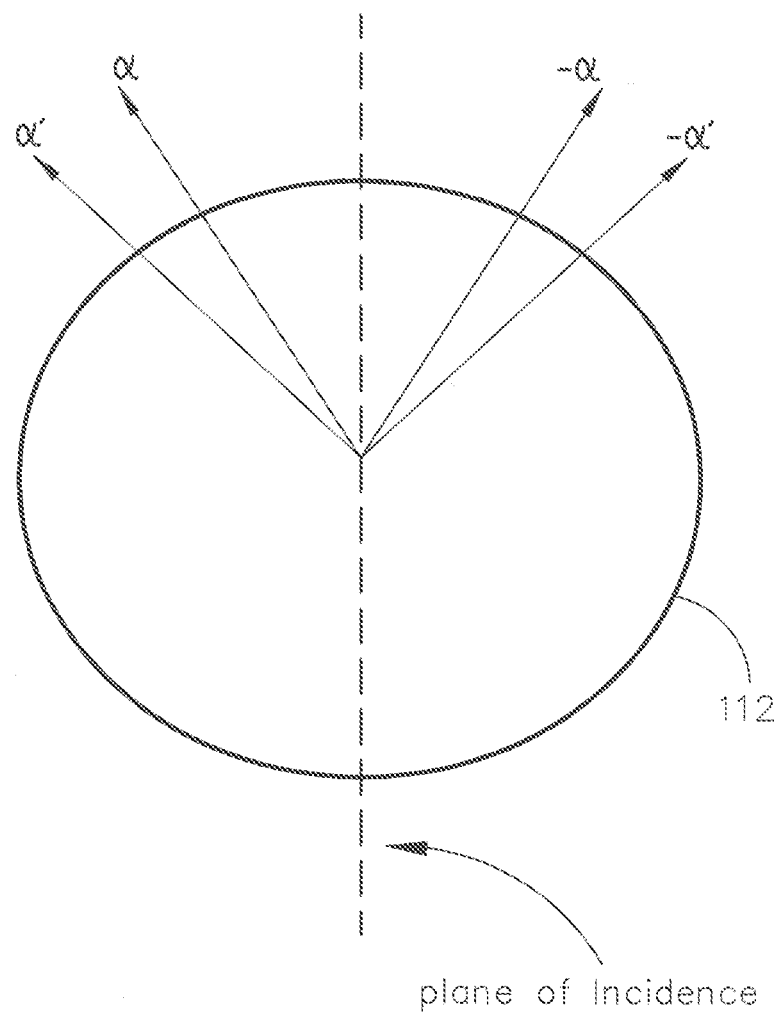
FIG. 2 is an illustration depicting multiple predetermined, discrete angular positions with respect to a cross-sectional view of a reflected beam.

Referring to FIGS. 1 and 2, illustrations depicting an ellipsometry system 100 in accordance to one embodiment of the present disclosure are shown. The ellipsometry system 100 may include a support mechanism 102 configured for supporting a wafer 104. The ellipsometry system 100 may also include an illumination source 106 configured for delivering an incident beam 108 through a polarizer 110 towards the wafer 104, illuminating at least a portion of the wafer 104. The incident beam 108 may be reflected off the wafer 104, forming a reflected beam 112 as shown in FIG. 1. The incident beam 108 and the reflected beam 112 span a plane commonly referred to as the plane of incidence.

The reflected beam 112 then passes a second polarizer, which is called an analyzer 114, and falls into a detector 116. The analyzer 114 and the detector 116 may be jointly referred to as the analyzer module, which is positioned along the optical path of the reflected beam 112 in the plane of incidence. In accordance with the present disclosure, multiple analyzer angles are utilized to collect ellipsometry data for a single measurement, therefore improving the stability of the ellipsometry system.

More specifically, ellipsometry data may be collected when the polarization direction of the analyzer 114 (vector A in FIG. 1) points to various predetermined, discrete angular positions. In one exemplary implementation, the direction of the analyzer 114 may be stepped/rotated from one discrete position to the next for each of the fixed angular positions, allowing the detector 116 to collect ellipsometry data at each fixed angular positions.

For instance, a pair of analyzer angles α and −α offset symmetrically on either side of the plane of incidence may be defined as the predetermined, discrete angular positions. The analyzer 114 may first be rotated so that the direction of the analyzer 114 (vector A) is pointing to the analyzer angle α. The detector 116 may collect the spectrum reflected off the wafer 104 passing through the analyzer 114 when vector A is pointing to the analyzer angle α. The direction of the analyzer 114 (vector A) may remain unchanged (i.e., pointing to the analyzer angle α) for a predetermined duration while the detector 116 is collecting the spectrum. Subsequently, the analyzer 114 may be rotated with respect to the reflected beam 112 so that the direction of the analyzer 114 (vector A) is pointing to the analyzer angle −α. The detector 116 may then collect the spectrum reflected off the wafer 104 passing through the analyzer 114 when vector A is pointing to the analyzer angle −α. The direction of the analyzer 114 (vector A) may remain unchanged (i.e., pointing to the analyzer angle −α) for the predetermined duration while the detector 116 is collecting the spectrum.

It is contemplated that the value of α may vary and may be determined for each specific application without departing from the spirit and scope of the present disclosure. Furthermore, the analyzer angles (i.e., the angular positions) are not limited to two depicted in the example above. More than two discrete angular positions may be defined without departing from the spirit and scope of the present disclosure.

It is also contemplated that the analyzer 114 is not required to be stepped from one discrete point to the next. In an alternative implementation, the analyzer 114 may continuously rotate through the range of angles and the detector 116 may collect the spectra reflected off the wafer 104 when the direction of the analyzer 114 (vector A) points to one of the predetermined analyzer angles. In yet another implementation, the analyzer 114 may continuously rotate through the range of angles and the detector 116 may collect the spectrum data reflected off the wafer 104, but only the data collected when the direction of the analyzer 114 (vector A) is pointing to one of the predetermined analyzer angles may be used/feed to subsequent processing steps (i.e., the data collected from other angles are not used).

The ellipsometry data collected in accordance with the present disclosure may be processed utilizing a processor module communicatively coupled with the detector 116. The processor module may be implemented as a processing unit, a computing device, an integrated circuit, or any control logic (stand-alone or embedded) in communication with the detector 116. The processor module may be located in proximity to the detector 116, or located elsewhere and communicate with the detector 116 via wired or wireless communication means.

The processor module may be configured for performing simultaneous regression of the ellipsometry data collected utilizing multiple analyzer angles as described above. For ellipsometry, model based measurement is the typical approach. The multiple spectra with different analyzer angle positions may be processed simultaneously for the better accuracy instead of averaging the measurement results with single analyzer angle spectrum. One of the advantages of the dual/multi analyzer angle measurements in accordance with the present disclosure is to minimize the systematic errors present in the optical design and mathematical model of the system such that the resultant errors after the model fit are symmetrically distributed around the ideal state of zero error, improving the stability of the ellipsometry system 100.

In addition, the processor module may also be configured to facilitate a calibration process to select the optimal angles for the analyzer 114. For instance, the analyzer 114 may be supported by a movable/rotatable mechanism. Initially, the direction of the analyzer 114 (vector A) may be setup to point to the angle α, then carefully tuning the second angle from the starting position of −α, in such a fashion as to maximize the symmetry of residual errors after the measurement model fit. That is, the two analyzer angles are not required to be exactly symmetric with respect to the plane of incidence.

It is further contemplated that an ellipsometry system may include more than one illumination source as described above for delivering additional incident beam(s) towards the wafer. Each illumination source may have a corresponding analyzer modules arranged in accordance with the present disclosure. It is understood that the arrangement of measurements with analyzer angles as described above may be independently configured for each illumination source. That is, if the ellipsometry system includes multiple ellipsometers each with a distinctive optical design, then it is appropriate for each subsystem to determine the optimum measurement analyzer angles in order to maximize its own sensitivity.

Furthermore, it is understood that the polarizer 110 may be configured as a continuously rotating polarizer. A continuously rotating polarizer may polarize the incident beam delivered to the wafer, effectively providing a spectroscopic ellipsometry system. The spectroscopic ellipsometry system may also utilize the multi-angle analyzer module in accordance with the present disclosure in order to improve its stability and sensitivity.

It is contemplated that the ellipsometry and spectroscopic ellipsometry systems in accordance with the present disclosure may provide improved stability, precision and sensitivity for inspecting various types of wafers including materials with high dielectric constant (also referred to as high-k applications). For such high-k applications, the value of α may range between 25° and 37°. However, it is understood that such a range may vary and may be determined for each specific application without departing from the spirit and scope of the present disclosure.

It is further contemplated that the ellipsometry and spectroscopic ellipsometry systems in accordance with the present disclosure may be implemented in combination with an apparatus of the type described in U.S. Pat. No. 5,608,526 and/or U.S. Pat. No. 6,813,026, which are hereby incorporated by reference as though fully set forth herein.

Figure 3:
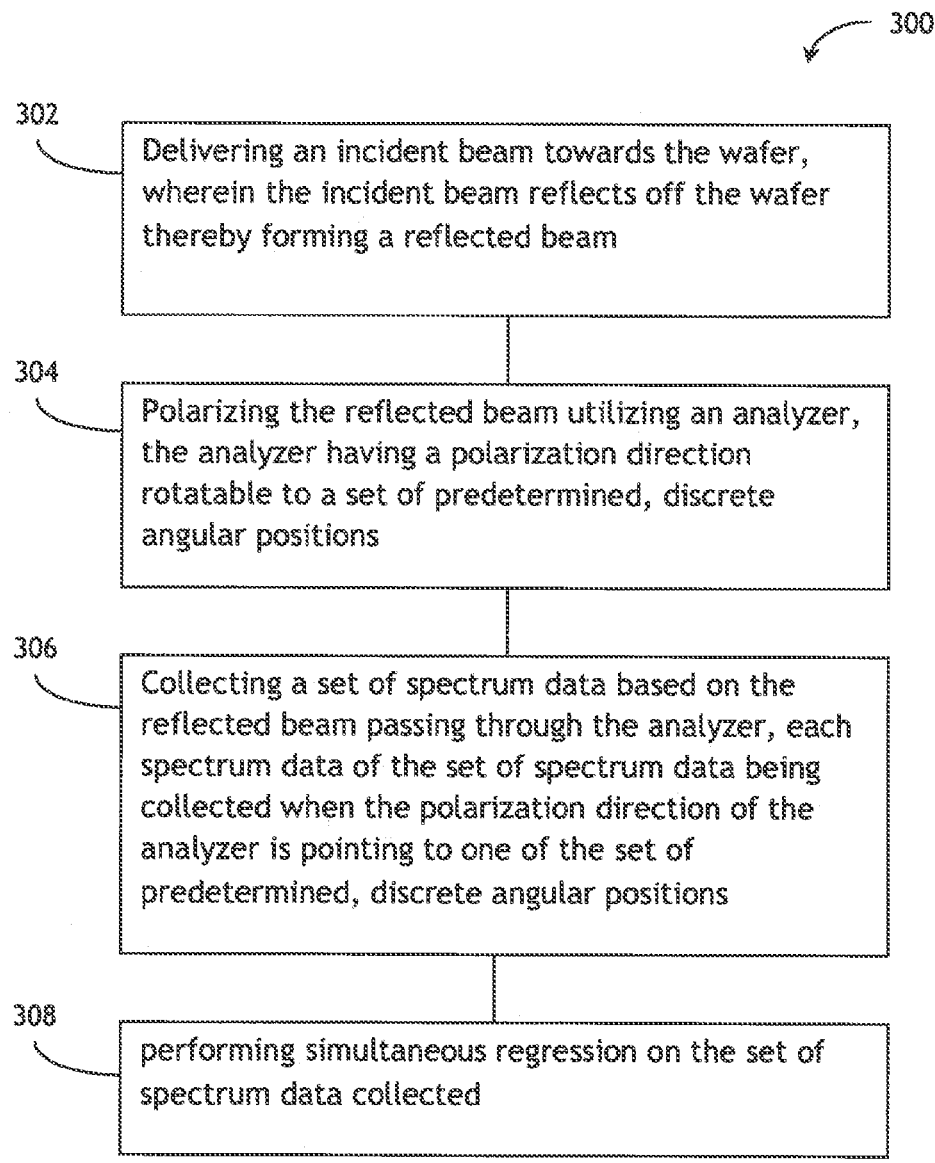
FIG. 3 is a flow chart illustrating an ellipsometry method for inspecting a wafer in accordance with the present disclosure.

Referring now to FIG. 3, an ellipsometry method 300 for inspecting a wafer is shown. Step 302 may deliver an incident beam towards the wafer. The incident beam may reflect off the wafer thereby forming a reflected beam as described above. The reflected beam may be polarized in step 304 utilizing an analyzer. The polarization direction of the analyzer may be rotatable to a set of predetermined, discrete angular positions. Step 306 may collect a set of spectrum data based on the reflected beam passing through the analyzer. Each spectrum data of the set of spectrum data being collected may correspond to one of the set of predetermined, discrete angular positions. Once the set of spectrum data is collected, step 308 may perform simultaneous regression on the set of spectrum data collected at these predetermined, discrete angular positions.

Figure 4:
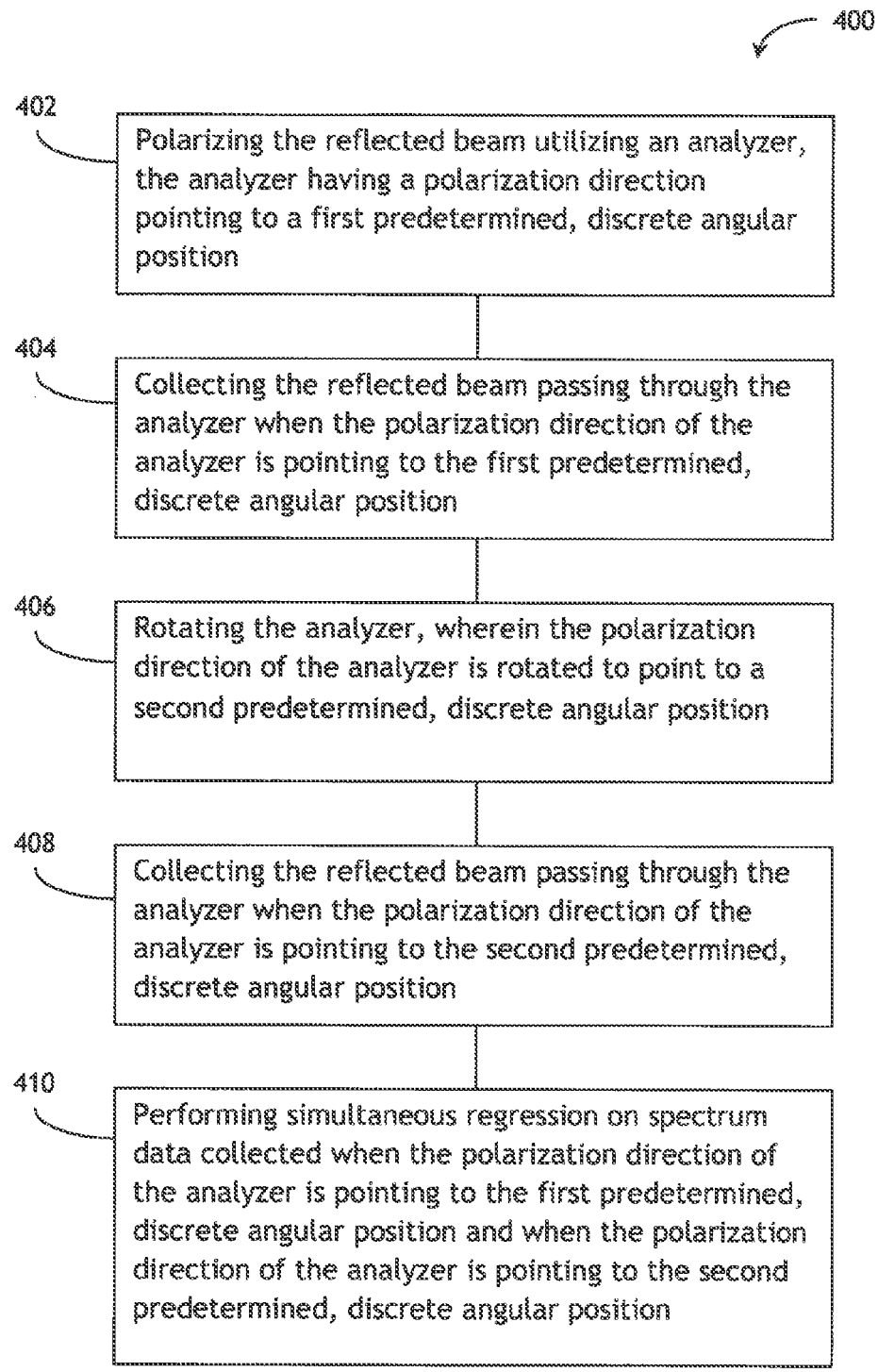
FIG. 4 is a flow chart illustrating a method for collecting spectrum data according to multiple predetermined, discrete angular positions.

It is contemplated that the set of spectrum data may be collected utilizing various approaches. In one exemplary approach, as illustrated in FIG. 4, step 402 may rotate the analyzer so that its polarization direction is pointing to a first predetermined, discrete angular position. Step 404 may then collect the reflected beam passing through the analyzer when the polarization direction of the analyzer is pointing to the first predetermined, discrete angular position. Subsequently, step 406 may rotate the analyzer so that its polarization direction is pointing to a second predetermined, discrete angular position. Step 408 may collect the reflected beam passing through the analyzer when the polarization direction of the analyzer is pointing to the second predetermined, discrete angular position. Step 410 may perform simultaneous regression on spectrum data collected when the polarization direction of the analyzer is pointing to the first predetermined, discrete angular position and when the polarization direction of the analyzer is pointing to the second predetermined, discrete angular position.

However, it is contemplated that the analyzer is not required to step from one discrete point to the next. In an alternatively implementation, the analyzer may continuously rotate through the range of angles and the detector may collect the spectrum data when the direction of the analyzer points to one of the predetermined analyzer angles. In yet another implementation, the analyzer may continuously rotate through the range of angles and the detector may collect the spectrum data reflected off the wafer, but only the data collected when the direction of the analyzer is pointing to one of the predetermined analyzer angles may be used for simultaneous regression.

It is contemplated that while the examples above referred to wafer inspections, the systems and methods in accordance with the present disclosure are applicable to other types of polished plates as well without departing from the spirit and scope of the present disclosure. The term wafer used in the present disclosure may include a thin slice of semiconductor material used in the fabrication of integrated circuits and other devices, as well as other thin polished plates such as magnetic disc substrates, gauge blocks and the like.

The methods disclosed may be implemented as sets of instructions, through a single production device, and/or through multiple production devices. Further, it is understood that the specific order or hierarchy of steps in the methods disclosed are examples of exemplary approaches. Based upon design preferences, it is understood that the specific order or hierarchy of steps in the method can be rearranged while remaining within the scope and spirit of the disclosure. The accompanying method claims present elements of the various steps in a sample order, and are not necessarily meant to be limited to the specific order or hierarchy presented.

It is believed that the system and method of the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory.

What is claimed is:

1. An ellipsometry system, comprising:
a support mechanism configured for supporting a wafer;
an illumination source configured for delivering an incident beam towards the wafer, wherein the incident beam reflects off the wafer thereby forming a reflected beam, the incident beam and the reflected beam define a plane of incidence;
an analyzer configured for polarizing the reflected beam, the analyzer having a polarization direction rotatable between two predetermined, discrete angular positions, the two angular positions being opposite with respect to the plane of incidence, wherein a first angular position corresponds to the plane of incidence offset by an acute offset angle α and a second angular position corresponds to the plane of incidence offset by approximately −α, and wherein the second angular position is calibrated by: generating a plurality of candidate angular positions each in proximity to an angular position of the plane of incidence offset by −α, and selecting one of the plurality of candidate angular positions as the second angular position, wherein the second angular position maximizes symmetry of residual errors with respect to the first angular position;
a detector configured for collecting a set of spectrum data based on the reflected beam passing through the analyzer, each spectrum data of the set of spectrum data being collected when the polarization direction of the analyzer is pointing to one of the two predetermined, discrete angular positions; and
a processor module configured for performing simultaneous regression on the set of spectrum data collected.

2. The ellipsometry system of claim 1, wherein the analyzer is configured to step between the two predetermined, discrete angular positions, wherein the polarization direction of the analyzer remains unchanged for a predetermined duration while the detector is collecting spectrum data at each angular position.

3. The ellipsometry system of claim 1, wherein the analyzer is configured to rotate continuously, and the detector is configured to collect spectrum data when the polarization direction of the analyzer is at one of the two predetermined, discrete angular positions.

4. The ellipsometry system of claim 1, wherein the two predetermined, discrete angular positions are pair-wise symmetric with respect to the plane of incidence.

5. The ellipsometry system of claim 1, wherein the acute offset angle α is between 25° and 37°.

6. The ellipsometry system of claim 1, wherein the illumination source further includes a rotatable polarizer, the rotatable polarizer configured for polarizing the incident beam being delivered towards the wafer.

7. An ellipsometry method for inspecting a wafer, the method comprising:
   delivering an incident beam towards the wafer, wherein the incident beam reflects off the wafer thereby forming a reflected beam, the incident beam and the reflected beam define a plane of incidence;
   polarizing the reflected beam utilizing an analyzer, the analyzer having a polarization direction rotatable to two predetermined, discrete angular positions, the two angular positions being opposite with respect to the plane of incidence, wherein a first angular position corresponds to the plane of incidence offset by an acute offset angle α and a second angular position corresponds to the plane of incidence offset by approximately −α, and wherein the second angular position is calibrated by: generating a plurality of candidate angular positions each in proximity to an angular position of the plane of incidence offset by −α, and selecting one of the plurality of candidate angular positions as the second angular position, wherein the second angular position maximizes symmetry of residual errors with respect to the first angular position;
   collecting a set of spectrum data based on the reflected beam passing through the analyzer, each spectrum data of the set of spectrum data being collected when the polarization direction of the analyzer is pointing to one of the two predetermined, discrete angular positions; and
   performing simultaneous regression on the set of spectrum data collected.

8. The ellipsometry method of claim 7, wherein the analyzer is configured to step from one of the two predetermined, discrete angular position to a next one of the two predetermined, discrete angular position, wherein the polarization direction of the analyzer remains unchanged for a predetermined duration while the detector is collecting spectrum data at each angular position.

9. The ellipsometry method of claim 7, wherein the analyzer is configured to rotate continuously, and the detector is configured to collect spectrum data when the polarization direction of the analyzer is at one of the two predetermined, discrete angular positions.

10. The ellipsometry method of claim 7, wherein the two predetermined, discrete angular positions are pair-wise symmetric with respect to the plane of incidence.

11. The ellipsometry method of claim 7, wherein the acute offset angle α is between 25° and 37°.

12. The ellipsometry method of claim 7, wherein the incident beam delivered towards the wafer is continuously polarized.

13. An ellipsometry method for inspecting a wafer, the method comprising:
   delivering an incident beam towards the wafer, wherein the incident beam reflects off the wafer thereby forming a reflected beam, the incident beam and the reflected beam define a plane of incidence;
   polarizing the reflected beam utilizing an analyzer, the analyzer having a polarization direction pointing to a first predetermined, discrete angular position, the first angular position corresponds to the plane of incidence offset by an acute offset angle α;
   collecting the reflected beam passing through the analyzer when the polarization direction of the analyzer is pointing to the first predetermined, discrete angular position, the polarization direction of the analyzer remains unchanged for a predetermined duration while the detector is collecting spectrum data at the first angular position;
   rotating the analyzer, wherein the polarization direction of the analyzer is rotated to point to a second predetermined, discrete angular position, the second angular position corresponds to the plane of incidence offset by approximately −α, and wherein the second angular position is calibrated by: generating a plurality of candidate angular positions each in proximity to an angular position of the plane of incidence offset by −α, and selecting one of the plurality of candidate angular positions as the second angular position, wherein the second angular position maximizes symmetry of residual errors with respect to the first angular position;
   collecting the reflected beam passing through the analyzer when the polarization direction of the analyzer is pointing to the second predetermined, discrete angular position, the polarization direction of the analyzer remains unchanged for a predetermined duration while the detector is collecting spectrum data at the second angular position; and
   performing simultaneous regression on spectrum data collected when the polarization direction of the analyzer is pointing to the first predetermined, discrete angular position and when the polarization direction of the analyzer is pointing to the second predetermined, discrete angular position.

14. The ellipsometry method of claim 13, wherein the first predetermined, discrete angular position and the second predetermined, discrete angular position are substantially symmetrical with respect to the plane of incidence defined.

15. The ellipsometry method of claim 13, further comprising:
   adjusting at least one of: the first predetermined, discrete angular position and the second predetermined, discrete angular position; and
   determining whether measurement sensitivities have been improved.

16. The ellipsometry method of claim 15, further comprising:
   continuously adjusting at least one of: the first predetermined, discrete angular position and the second predetermined, discrete angular position until the measurement sensitivities are maximized.

17. The ellipsometry method of claim 13, wherein the incident beam delivered towards the wafer is continuously polarized.

18. The ellipsometry method of claim 13, further comprising:
   rotating the analyzer, wherein the polarization direction of the analyzer is rotated to point to a third predetermined, discrete angular position;

collecting the reflected beam passing through the analyzer when the polarization direction of the analyzer is pointing to the third predetermined, discrete angular position; and performing simultaneous regression on spectrum data collected when the polarization direction of the analyzer is pointing to the first predetermined, discrete angular position, when the polarization direction of the analyzer is pointing to the second predetermined, discrete angular position, and when the polarization direction of the analyzer is pointing to the third predetermined, discrete angular position.

* * * * *